United States Patent [19]

Spitzner

[11] 4,252,959
[45] Feb. 24, 1981

[54] SULFONYLHYDRAZINES, METAL COMPLEXES THEREOF, AND SOLUTIONS CONTAINING SUCH COMPOUNDS FOR USE IN EXTRACTION OF METAL VALUES

[75] Inventor: Ernest Spitzner, Minneapolis, Minn.

[73] Assignee: Henkel Corporation, Minneapolis, Minn.

[21] Appl. No.: 53,116

[22] Filed: Jun. 28, 1979

[51] Int. Cl.³ .......................................... C07D 213/77
[52] U.S. Cl. .................................. 546/306; 546/162; 548/152; 423/24; 423/101
[58] Field of Search .................................. 546/306, 2; 423/DIG. 14

[56] References Cited

U.S. PATENT DOCUMENTS 4,160,807  7/1979  Virnig et al. ........................ 423/139

*Primary Examiner*—Alan L. Rotman
*Attorney, Agent, or Firm*—Patrick J. Span

[57] ABSTRACT

Certain sulfonylhydrazines, metal complexes thereof and solutions of said compounds in essentially water-immiscible, liquid hydrocarbon solvents are disclosed. The sulfonylhydrazines have the general structural formula:

$$R-SO_2NHNH-R_1$$

wherein R and $R_1$ are as defined in the specification and claims hereof. Particular metal values are recovered from their aqueous solutions by using sulfonylhydrazines dissolved in essentially water-immiscible, liquid hydrocarbon solvents. The extraction process involves contacting the metal value containing aqueous solution with the solution of the sulfonylhydrazines in essentially water-immiscible, liquid hydrocarbon solvent and stripping the metal from the loaded organic phase.

17 Claims, No Drawings

SULFONYLHYDRAZINES, METAL COMPLEXES THEREOF, AND SOLUTIONS CONTAINING SUCH COMPOUNDS FOR USE IN EXTRACTION OF METAL VALUES

The present invention is directed to novel sulfonylhydrazines, organic solvent solutions thereof, metal complexes of such sulfonylhydrazines, organic solvent solutions of such complexes and the method of using said sulfonylhydrazines to extract metal values from aqueous solution.

Liquid ion exchange recovery of metal values from aqueous solutions thereof has in the past ten years or so become a mature commercial operation. Briefly, liquid ion exchange processes function by transfering a metal value from Phase A (aqueous) to Phase B (organic) and thence from Phase B to Phase C (aqueous). However, complexities of liquid ion exchange arise in a number of areas including (1) synthesis and manufacture of the reagent system, (2) evaluation of the system's capabilities and (3) engineering application leading to large scale metal recovery.

The key to a successful application of liquid ion exchange is the reagent. In this respect, the reagent should desirably meet a number of criteria. In the first instance, the reagent should complex with or react with a metal or group of metals and such complexing or reaction should be relatively fast in order to avoid having to use large holding tanks or reaction vessels. It is also desirable that the reagent exhibits preference for a single metal where the aqueous starting solutions contain a number of metal values. Such selectivity can often be optimized at designated pH ranges. The reagent should also desirably complex or react quantitatively with the metal under the extraction conditions. Additionally, the reagent, as well as the resulting metal complex, must exhibit satisfactory solubility in the essentially water-immiscible organic solvent being used. Further, the reagent-metal reaction or complexing should be reversible so that the metal can be stripped from the organic phase. For economic reasons, the reagent should be relatively stable so that it can be recycled repeatedly. Also, it should be essentially water insoluble to prevent significant loss into the aqueous phase or phases. Furthermore, the reagent should not cause or stabilize emulsions. Again and principally for economic reasons, the reagent should not react with or load significant quantities of acid, for example, from aqueous acidic stripping solutions. And, of course, the cost of the reagent should be such that the liquid ion exchange process can be operated at a profit.

Of significant, but lesser, importance, is the selection of the essentially water-immiscible solvent to be used in the liquid ion exchange process. Such selection is important principally from a cost standpoint, especially in the recovery of the more common metals. Existing commercial operations for copper recovery, for example, generally employ aliphatic kerosenes because of the low cost thereof. Thus, the cost of the reagent and the solvent is intertwined in providing the desired overall economics of the process being commercialized.

One of the most extensively used systems in commercial operation in the last decade for copper recovery has employed benzophenoximes or combination reagents including a benzophenoxime component. While being economic, improvements can be made since the said benzophenoximes do not have total selectivity for copper over iron, for example. Other types of reagents have been proposed for use in copper recovery including the alkenyl substituted 8-hydroxyquinolines.

It has now been discovered that certain novel sulfonylhydrazines, as more fully defined hereinafter, are useful in liquid ion exchange recovery processes. The new compounds of the present invention are represented by the following general structural formula:

$$R-SO_2NHNH-R_1$$

wherein R is a radical selected from the group consisting of alkyl, aryl, alkararyl and aralkyl, in which the alkyl groups are linear or branched chain and wherein $R_1$ is a heterocyclic radical selected from the group consisting of pyridine, quinoline and benzothiazole. The linear or branched chain alkyl groups will generally contain from 1 to 20 carbon atoms. Moreover, it is generally preferred that the compounds of the invention possess at least one alkyl group containing at least eight carbon atoms. Dodecylbenzene is typical of the preferred groups represented by R in the general structural formula.

The compounds of the present invention are also characterized as having solubilities in essentially water-immiscible liquid hydrocarbon solvents of at least 2% by weight. Correspondingly, they are further characterized in that the copper (Cu++) complexes of the compound have solubilities of at least 2% by weight in the said water-immiscible, liquid hydrocarbon solvents. Especially preferred compounds of the invention are those which exhibit solubilities of at least 2% by weight in both pure and complexed form, in aliphatic or aromatic hydrocarbons, or mixtures thereof, having flash points of at least 150° F. Thus, the compounds of the invention may preferably be further characterized as having substituents containing a sufficient number of carbon atoms and/or branching in the alkyl chains to provide at least the minimum 2% solubility in the aforementioned solvents.

The aforementioned preference for alkyl substituents containing at least 8 carbon atoms and/or possessing a branched chain structure is due to their contribution to the solubilities of the compounds in the above-described solvents. The beneficial effect provided by the number of carbon atoms is obtained by having an alkyl substituent of at least 8 carbon atoms or more than one alkyl substituent in which the sum of the carbon atoms is at least 8. Accordingly, the most preferred compounds of the present invention are those possessing one or more branched chain alkyl substituents having at least 8 carbon atoms or those possessing branched chain alkyl substituents in which the sum of the carbon atoms is at least 8.

Thus, according to preferred embodiments, the sulfonylhydrazines of the invention have the general structural formula:

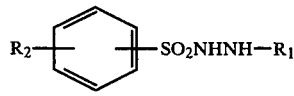

wherein $R_1$ is as previously defined and $R_2$ is a linear or branched chain alkyl containing at least 8 carbon atoms. Of these compounds those in which $R_2$ is dodecyl have been found to be particularly effective in extracting metal values from aqueous solutions. Typical of these compounds are 2-(dodecylbenzenesulfonylhydrazino)-pyridine having the structure:

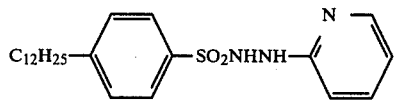

2-(dodecylbenzenesulfonylhydrazino)quinoline having the structure:

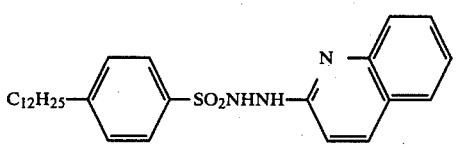

8-(dodecylbenzenesulfonylhydrazino)quinoline having the structure:

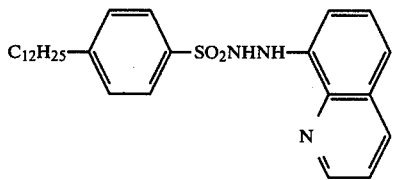

and 2-(dodecylbenzenesulfonylhydrazino)benzothiazole having the structure:

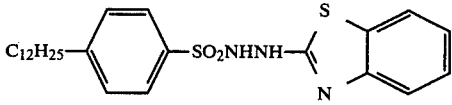

However, it should be understood that as the utility of the compounds of the invention resides in their ability to extract metal values from aqueous solutions, various substituents which do not interfere with chelation may be appended without departing from the scope of the invention. Illustrative of such substituents are electron withdrawing groups, e.g., halogen nitrile, nitro, trifluoromethyl, ester and the like. Additionally, certain other radicals may be substituted for those described above as $R_1$ notably 2-hydroxyethyl, —$CH_2CH_2OH$. However, for purposes of this application, the heterocyclic species is preferred.

The sulfonylhydrazines of the invention are prepared by reaction of the appropriate hydrazines with a substituted sulfonyl chloride according to the reaction:

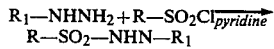

The substituted sulfonyl chloride may be prepared from substituted sulfonic acids by reaction with thionyl chloride. In the Examples which follow the dodecylbenzenesulfonylchloride was prepared as in Example I-A of U.S. Pat. No. 4,100,163, the disclosure of which is incorporated herein by reference.

Further details of the synthesis of the compounds of the invention are found in the Examples which follow the description of the invention.

The process of the present invention is a liquid ion exchange process in which any one of the sulfonylhydrazine compounds of the invention is dissolved in an essentially water-immiscible, liquid hydrocarbon solvent and the resulting solution is contacted with a metal containing aqueous phase to extract at least a portion of the metal values into the organic phase. The phases are then separated and metal values are stripped from the loaded organic phase by use of an aqueous stripping medium.

A wide variety of essentially water-immiscible, liquid hydrocarbon solvents can be used in the metal recovery process of the present invention. These include: aliphatic and aromatic hydrocarbons such as kerosenes, benzene, toluene, xylene and the like. The choice of the said essentially water-immiscible liquid hydrocarbon solvent for particular commercial operations will depend on a number of factors including the design of the solvent extraction plant (i.e., mixer-settlers, Podbielniak extractors, etc.), the value of the metal being recovered, disposal of plant effluent and the like. The process of the present invention finds particular use in the extraction recovery of the major, non-ferrous, transition metals—i.e., copper, nickel, zinc, cobalt(II) and cobalt(III), as will be described more fully hereinbelow. Essentially, all of the major plants in operation currently for the recovery of these metals (particularly $Cu++$) use mixer-settlers, with relatively large organic inventories and some loss of solvent invariably occurs by evaporation, entrainment in the aqueous and the like. Under these circumstances, preferred solvents for use in the metal recovery processes of the present invention are the aliphatic and aromatic hydrocarbons having flash points of 150° F. and higher and solubilities in water of less than 0.1% by weight. These solvents are also essentially non-toxic and chemically inert and the costs thereof are currently within practical ranges—i.e., normally less than one dollar (U.S.) per gallon to as low as thirty cents (U.S.) or so. Representative commercially available solvents are Kermac 470B (an aliphatic kerosene available from Kerr-McGee—Flash Point 175° F.), Chevron Ion Exchange Solvent (available from Standard Oil of California—Flash Point 195° F.), Escaid 100 and 110 (available from Exxon-Europe—Flash Point 180° F.), Norpar 12 (available from Exxon-U.S.A.—Flash Point 160° F.), Conoco C-1214 (available from Conoco—Flash Point 160° F.), Aromatic 150 (an aromatic kerosene available from Exxon-U.S.A.—Flash Point 150° F.) and various other kerosenes and petroleum fractions available from other oil companies.

The present invention thus additionally relates to new compositions wherein the sulfonylhydrazine compounds of the invention are dissolved in the essentially water-immiscible, liquid hydrocarbon solvents described above. In this regard, liquid ion exchange reagents are often sold as solutions in organic solvents. These new compositions consist essentially of solutions of at least 2% by weight of the sulfonylhydrazines in essentially water-immiscible, liquid hydrocarbon solvents. When sold as concentrates, the solutions will preferably contain from about 25 to 75% by weight of the sulfonylhydrazines.

In the process of the present invention, the organic solvent solutions will preferably contain from about 2 to 75% by weight of the sulfonylhydrazine compounds and even more preferably from about 5 to 20% by weight thereof. Additionally, volume ratios of the organic:aqueous phase vary widely since the contacting of any quantity of the reagent solution with the metal containing aqueous phase will result in extraction of metal values into the organic phase. However, for commercial practicality, the organic:aqueous phase ratios are preferably in the range of about 5:1 to 1:5. For practical purposes, the extracting and stripping are normally conducted at ambient temperatures and pressures although higher or lower temperatures and/or pressures are entirely operable. Most advantageously, the entire process can be carried out continuously with the stripped organic solvent solution being recycled for contacting further quantities of metal containing solutions.

The present invention also relates to the metal complexes of the sulfonylhydrazine compounds and to the essentially water-immiscible, liquid hydrocarbon solvent solutions thereof. The solutions consist essentially of the said solvent and at least 2% by weight, and preferably less than 75% by weight, of the metal complexes. While not normally practiced in the industry, the solutions of the metal complexes can be obtained at one location and transported to another for stripping as hereinafter described. The term "metal complex" as used herein is meant to connote compositions of the sulfonylhydrazines with other than insignificant quantities of metal ions. Although the exact structural nature of these complexes has not been ascertained, indications are that under conditions of maximum loading, particularly with $Cu++$ and $Zn++$ metal ions, the complexes comprise the metal and sulfonylhydrazine compound generally in a molar ratio of 1:2. Maximum loading, however, is not required for achieving acceptable performance in liquid ion exchange processes and hence the metal complexes are generally defined as including the designated metals in more than insignificant quantities up to maximum loading.

The metal recovery process of the present invention is useful for the recovery of the following metal values from their aqueous solutions: $Cu++$, $Ni++$, $Zn++$, $Co++$ and $Co+++$. These metal values are all transition metals in Groups Ib, IIb, and VIII. The extraction of these various metals from aqueous solutions depends upon a number of factors, including, for example, the concentration of the metal ion, the particular anions present, and the pH of and/or ammonia concentration in the aqueous solutions, as well as the particular sulfonylhydrazine selected and its concentration in the organic phase. Generally, it is preferred to extract the metal values from ammoniacal solutions in which the preferred concentrations of ammonia is from about 10 to 150 g/l. However, it is understood that for each aqueous metal solution and reagent solution there will be a preferred or optimum set of extraction conditions, and those skilled in the art, based on the information given herein, especially in the examples to follow, will be able, after a limited number of trial runs, to determine such preferred or optimum conditions for the respective systems under consideration. This is equally true of the stripping operations. By the term "stripping" is meant the transfer of at least a portion of the metal values in the loaded organic phase to the aqueous stripping medium. The metal values so stripped are desirably recovered from the aqueous stripping medium by conventional techniques, preferably electrolysis. The volume ratios of loaded organic:aqueous stripping phase can also vary widely. However, the overall object of the process is to provide a metal containing stripping solution of known composition and concentration suitable for conventional recovery techniques such as electrolysis. Accordingly, the metal will preferably be present in higher concentrations in the aqueous stripping medium than in the strating metal containing solution. To accomplish this, the loaded organic:aqueous stripping medium phase ratio will normally be in the range of about 1:1 to 10:1. The stripping medium is preferably an aqueous mineral acid solution such as 25 to 250 g/l $H_2SO_4$.

While the process of the present invention has been described as particularly effective in extracting $Cu++$, $Ni++$, $Zn++$, $Co++$ and $Co+++$, metal values from aqueous solutions, it may also be applied to extract other chemically similar metal values, such as $Cd++$, $Hg++$, $Ag+$ and $Pb++$. They have also been found to be mildly effective in extracting uranium, molybdenum, vanadium and iron. The process of the invention thus provide a simple, continuous method of extracting valuable metal values from aqueous solutions. Of equal importance is the economic advantages attendant from the process which allows the extracting reagent to be stripped of metal values and recycled for subsequent loading.

To further illustrate various aspects of the invention, the following Examples are provided. However, it is understood that as their purpose is entirely illustrative, they are in no way intended to limit the scope of the invention.

EXAMPLE 1

Preparation of 2-(dodecylbenzenesulfonylhydrazino)-pyridine

Starting Materials: 2.4 g (0.022 mol) 2-hydrazinopyridine 6.9 g (0.02 mol) dodecylbenzenesulfonylchloride 2.5 g (0.025 mol) triethylamine 20 ml tetrahydrofuran To a solution of the dodecylbenzenesulfonylchloride in 10 tetrahydrofuran was added a solution of the hydrazinopyridine and triethylamine in 10 ml tetrahydrofuran. The reaction mixture was maintained below 10° C. in an ice bath until the addition of the second solution was complete and thence for 30 minutes longer while the mixture was continuously stirred. The mixture was then treated with Skelly B solvent. The Skelly B solution was washed three times with an aqueous solution of sodium chloride, dried over magnesium sulfate, filtered and evaporated to give 8.2 g of a dark orange syrup. Nuclear magnetic resonance (NMR) and infra-red (IR) analysis confirmed the product to be 2-(dodecylbenzenesulfonylhydrazino)pyridine.

EXAMPLE 2

Preparation of 2-(dodecylbenzenesulfonylhydrazino)-quinoline

Starting Materials: 3.1 g (0.02 mol) of 2-hydrazinoquinoline 6.9 g (0.02 mol) dodecylbenzenesulfonylchloride 40 ml tetrahydrofuran 4 ml dimethylformamide 2.5 g (0.025 mol) triethylamine To a solution of the sulfonyl chloride in 10 ml tetrahydrofuran was added a solution of the hydrazinoquinoline and triethylamine in 30 ml tetrahydrofuran (4 ml dimethylformamide was included to aid solubility). The temperature of the reaction mixture was maintained below 10° C. during the addition and for 30 minutes thereafter while the mixture was continuously stirred. The product was recovered as in Example 1 yielding 8.4 g of a tan solid. NMR and IR analysis confirmed the product to be 2-(dodecylbenzenesulfonylhydrazino)quinoline.

EXAMPLE 3

Preparation of 8-(dodecylbenzenesulfonylhydrazino)-quinoline

Starting Materials: 3.2 g (0.02 mol) 8-hydrazinoquinoline 6.9 g (0.02 mol) dodecylbenzenesulfonylchloride 2.5 g (0.025 mol) triethylamine 30 ml tetrahydrofuran The starting materials were combined as in the previous Examples and the resulting reaction mixture was stirred for one hour while being maintained at a temperature below 10° C. Diethyl ether and water were added, the layers were separated and the aqueous layer was extracted with diethyl ether. The organic solutions were then combined, washed twice with a 6% ammonia solution, three times with an aqueous sodium chloride solution, dried over magnesium sulfate, filtered and evaporated to give 8.2 g of a dark red syrup. NMR and IR analysis confirmed the product to be 8-(dodecylbenzenesulfonylhydrazino)quinoline.

The 8-hydrazinoquinoline was prepared by the method of A. Krasavin, et al., Metody Polucheniya Khim. Reaktivov i Preparatov, Gos. Kom. Sov. Min. SSSR po Khim., No. 7, 5(1963) as described in Chem. Abstr., 61, 3070 (1964).

Preparation of 8-Hydrazinoquinoline

Starting Materials: 72.6 g (0.5 mole) 8-hydroxyquinoline 165.0 g (5.0 mole) hydrazine, 97% 85.0 g (4.7 mole) water A solution of hydrazine in water (equivalent to 250 ml of 100% hydrazine hydrate) was added to the 8-hydroxyquinoline and the mixture was refluxed under nitrogen for 68 hours. After cooling to about 40° C., brine was added and the mixture was extracted with benzene. The benzene solution was washed once with brine, three times with Claisen's alkali (prepared by dissolving 35 g of potassium hydroxide in 25 ml of water, cooling, and adding 100 ml of methanol), twice again with brine, dried over magnesium sulfate, filtered and evaporated to give 60.0 g of an orange oil which crystallized on standing. IR and NMR analysis confirmed the product to be 8-hydrazinoquinoline.

EXAMPLE 4

Preparation of 2-(dodecylbenzenesulfonylhydrazino)-benzothiazole

Starting Materials: 3.3 g (0.02 mol) 2-hydrazinobenzothiazole 6.9 g (0.02 mol) dodecylbenzenesulfonylchloride 2.5 g (0.025 mol) triethylamine 35 ml dimethylformamide To a solution of the sulfonylchloride in 10 ml dimethylformamide was added a solution of the hydrazinobenzothiazole and triethylamine in 25 ml dimethylformamide. The temperature of the reaction mixture was maintained below 10° C. during the addition and for 30 minutes thereafter during which time it was continuously stirred. The product was recovered in the manner described previously in Examples 1 and 2. Nmr and IR analysis confirmed the product to be 2-(dodecylbenzenesulfonylhydrazino)-benzothiazole.

EXAMPLE 5

Extraction of Metal Values

To determine the ability of the various sulfonylhydrazine compounds of the present invention to extract metal values from aqueous solutions, tests were conducted in accordance with the following procedures.

A 0.1 molar solution of a sulfonylhydrazine compound in an identified essentially water-immiscible liquid hydrocarbon solvent and five aqueous solutions of the following compositions were used:

| Metal | Composition |
|---|---|
| $Cu^{++}$ | 0.05 M $CuSO_4$ (3.2 g/l $Cu^{++}$), 0.4 M $NH_3$, and 0.1 M $(NH_4)_2SO_4$ |
| $Ni^{++}$ | 0.05 M $NiSO_4$ (2.0 g/l $Ni^{++}$), 0.4 M $NH_3$, and 0.1 M $(NH_4)_2SO_4$ |
| $Zn^{++}$ | 0.05 M $ZnSO_4$ (3.2 g/l $Zn^{++}$), 0.4 M $NH_3$, and 0.1 M $(NH_4)_2SO_4$ |
| $Co^{++}$ | 0.025 M $CoSO_4$ (1.5 g/l $Co^{++}$) 1.7 M $NH_3$, and 0.1 M $(NH_4)_2SO_4$ prepared as needed under an atmosphere of nitrogen |
| $Co^{+++}$ | 0.25 M $CoSO_4$ (1.5 g/l $Co^{++}$), 1.7 M $NH_3$, and 0.1 M $(NH_4)_2CO_3$ (air oxidized to $Co^{+++}$) |

Portions of the organic solution were shaken with the five aqueous solutions at an organic:aqueous phase volume ratio of 1:1 for one hour at ambient temperature. The organic phases were then analyzed for metal content. If a third phase was present, both the organic and aqueous phases were clarified and analyzed. Table A summarizes the data obtained from the extraction tests for various sulfonylhydrazine reagents of the present invention. In the table all concentrations are given in g/l.

TABLE A**

| REAGENT | SOLVENT* | [Cu++] | [Ni++] | [Zn++] | [Co++] | [Co+++] |
|---|---|---|---|---|---|---|
| 2-(dodecylbenzene-sulfonylhydrazino)-pyridine | Solvesso 150 | 1.50 | 2.22 | 1.05 | 1.01 | 0.855 |
| 2-(dodecylbenzene-sulfonylhydrazino)-quinoline (ppt'd after 1 week) | Solvesso 150 | 1.53 | Aq. 0.900 | 1.38 | Aq. 0.013 | 0.395 |
| 8-(dodecylbenzene-sulfonylhydrazino)-quinoline | Solvesso 150 | 1.39 | 1.71 | 0.85 | 1.15 | 1.2 |
| 2-(dodecylbenzene-sulfonylhydrazino)-benzothiazole | Solvesso 150 | 0.515 | 1.09 | 2.28 | 0.97 | 0.596 |

*Solvesso 150 is an aromatic kerosene having a flash point of 150° F.
**All analyses on organic unless otherwise stated.

EXAMPLE 6 pH Isotherms

To determine the extent of extraction of various metal ions as a function of pH, tests were conducted as follows. Portions of a 0.1 molar solution of a particular sulfonylhydrazine in an identified essentially water-immiscible liquid hydrocarbon solvent were shaken with aqueous solutions composed of equivolumes of the following components:

Component A—0.2 M metal sulfate solution in water
Component B—water or sulfuric acid or sodium hydroxide solutions ranging from 0.01 to 0.1 M Component B was selected in such a manner as to insure the desired pH of the aqueous raffinate. In each test, the organic solution and aqueous solution were shaken at an organic:aqueous phase volume ratio of 1:1 for one hour at ambient temperature. Subsequent analysis of the organic phase for metal content and the aqueous phase for pH generated the data contained in Tables B and C which demonstrates the degree of metal extraction as a function of pH for the particular reagent systems under study. In the Tables, concentrations are given in grams per liter unless otherwise indicated.

TABLE B 2-(dodecylbenzenesulfonylhydrazino)pyridine in Solvesso 150

| [Cu] | AQ pH | [Ni] | AQ pH |
|---|---|---|---|
| .018 | .66 | .009 | .68 |
| .520 | 1.39 | <.005 | 1.44 |
| 1.20 | 1.88 | .021 | 3.88 |
| 1.77 | 2.79 | .980 | 5.77 |
| 2.35 | 4.77 | 2.06 | 7.32 |

TABLE C 8-(dodecylbenzenesulfonylhydrazino)quinoline in Solvesso 150

| [Ni] | AQ pH |
|---|---|
| .007 | .64 |
| .007 | 1.39 |
| .135 | 3.98 |
| 1.73 | 5.55 |
| 3.12 | 7.16 |

EXAMPLE 7

Ammonia Isotherms

To determine the extent of extraction of various metal ions as a function of total ammonia concentration in the aqueous phase, tests were conducted in accordance with the following procedure. Portions of a 0.1 molar solution of a particular sulfonylhydrazine compound in Solvesso 150 solvent were shaken at 1:1 organic:aqueous phase volume ratio for approximately one hour at ambient temperature with aqueous ammoniacal solutions containing a particular metal ion. The organic phase was then separated and analyzed for metal concentration, generating the data contained in Tables D, E and F which demonstrate the degree of metal extraction as a function of ammonia concentration for particular reagent systems. In the Tables, all concentrations are given in grams per liter.

TABLE D 2-(dodecylbenzenesulfonylhydrazino)pyridine in Solvesso 150

| [NH3] | [Cu] AQ Feed | [Cu] | % Extraction |
|---|---|---|---|
| 15.1 | .316 | .322 | 100 |
| 29.9 | .311 | .324 | 100 |
| 55.4 | .316 | .314 | 99 |
| 85.1 | .314 | .256 | 82 |
| 104.0 | .320 | .168 | 52 |
| 141.9 | .343 | .127 | 37 |

| [NH3] | [Ni] AQ Feed | [Ni] | % Extraction |
|---|---|---|---|
| 15.1 | .347 | .300 | 86 |
| 30.0 | .357 | .295 | 82 |
| 60.0 | .359 | .305 | 85 |
| 89.5 | .369 | .295 | 79 |
| 118.0 | .378 | .262 | 69 |
| 149.6 | .374 | .195 | 52 |

TABLE E 8-(dodecylbenzenesulfonylhydrazino)quinoline in Solvesso 150

| [NH3] | [Cu] AQ Feed | [Cu] | % Extraction |
|---|---|---|---|
| 15.1 | .316 | .260 | 82 |
| 29.9 | .311 | .210 | 67.5 |
| 55.4 | .316 | .178 | 56 |
| 85.1 | .314 | .148 | 47 |
| 104.1 | .320 | .130 | 41 |
| 141.9 | .343 | .108 | 31 |

| [NH3] | [Ni] AQ Feed | [Ni] | % Extraction |
|---|---|---|---|
| 15.1 | .347 | .296 | 85 |
| 30.0 | .357 | .270 | 75 |
| 60.0 | .359 | .164 | 45 |
| 89.5 | .369 | .092 | 24 |
| 118.6 | .378 | .061 | 16 |
| 149.6 | .374 | .038 | 10 |

TABLE F 2-(dodecylbenzenesulfonylhydrazino)benzothiazole in Solvesso 150

| [NH3] | [Ni] AQ Feed | [Ni] | % Extraction | [NH3] | [Zn] AQ Feed | [Zn] | % Extraction |
|---|---|---|---|---|---|---|---|
| 15.1 | .347 | .300 | 86 | 14.4 | .330 | .305 | 92 |
| 30.0 | .357 | .283 | 79 | 28.9 | .332 | .260 | 78 |
| 60.0 | .359 | .205 | 57 | 58.3 | .332 | .121 | 36 |
| 89.5 | .369 | .150 | 41 | 87.2 | .332 | .064 | 19 |
| 118.6 | .378 | .086 | 23 | 116.2 | .331 | .044 | 13 |
| 149.6 | .374 | .056 | 15 | 147.0 | .331 | 0.27 | 8 |

EXAMPLE 8

Acid Stripping, Ammonia Loading and Acid Loading

In order to determine (1) the extent of metal stripping as a function of acid concentration, (2) the extent of ammonia loading during extraction and (3) the extent of acid loading during stripping, the following tests were conducted. A 0.1 M solution of the particular sulfonylhydrazine compound in Solvesso 150 and aqueous solutions having the following compositions were prepared.

(A) a 0.1 M metal sulfate, 0.6 M NH3 and 0.15 M (NH4)2SO4 solution in water.

(B) 0, 25, 50, 100 and 150 gpl H2SO4 solutions in water.

In the first step, the reagent solution was shaken with aqueous solution A at an organic:aqueous phase volume ratio of 1:2 for one hour at ambient temperature. The phases were separated and the loaded organic phase was contacted a second time as before with fresh aqueous solution A. The resulting organic phase was separated and analyzed for metal concentration. The loaded organic phase was then shaken with solution B at an organic:aqueous phase ratio of 1:1 for one hour at ambient temperature. The phases were then separated and the organic phase was analyzed for metal content while the aqueous phase was analyzed for ammonia concentration. Next, the stripped organic phase was washed with water at an organic:aqueous phase ratio of 1:1 for one hour and analyzed for $H_2SO_4$ concentration. The results of this procedure are disclosed in Tables G and H. All concentrations are given in grams per liter.

TABLE G 2-(dodecylbenzenesulfonylhydrazino)pyridine in Solvesso 150

| METAL | ACID CONC g/l | | | | |
|---|---|---|---|---|---|
| | 0 | 25 | 50 | 100 | 150 |
| [Cu] | 2.23 | .34 | .275 | .077 | .030 |
| % Stripping | 0 | 85 | 88 | 97 | 99 |
| [NH₃] Aq Scrub | — | .051 | — | — | .065 |
| pH Aq Scrub | — | 2.18 | 1.95 | — | 1.19 |
| [Ni] | 1.76 | .570 | .465 | .550 | .240 |
| % Stripping | 0 | 68 | 74 | 69 | 86 |
| [NH₃] Aq Scrub | — | .425 | .391 | .476 | .493 |
| pH Aq Scrub | — | 5.28 | 4.41 | 4.66 | 2.00 |

TABLE H 8-(dodecylbenzenesulfonylhydrazino)quinoline in Solvesso 150

| METAL | ACID CONC g/l | | | | |
|---|---|---|---|---|---|
| | 0 | 25 | 50 | 100 | 150 |
| [Cu] | 2.24 | .800 | .560 | .353 | .239 |
| % Stripping | 0 | 64 | 75 | 84 | 89 |
| [NH₃] Aq Scrub | — | 2.55 | — | — | 1.36 |
| pH Aq Scrub | — | 3.31 | 3.04 | 2.12 | .92 |
| [Ni] | 1.90 | .388 | .266 | .256 | .185 |
| % Stripping | 0 | 80 | 86 | 87 | 90 |
| [NH₃] Aq Scrub | — | .85 | .82 | 1.17 | 1.12 |
| pH Aq Scrub | — | 2.19 | 1.17 | 1.12 | 1.19 |

While the present invention has now been described in terms of certain preferred embodiments, and exemplified with respect thereto, the skilled artisan will readily appreciate that various modifications, changes, omissions, and substitutions may be made without departing from the spirit thereof. It is intended, therefore, that the present invention be limited solely by the scope of the following claims.

What is claimed is:

1. A compound of the structure:

wherein R is a member selected from the group consisting of alkyl, aryl, alkaryl and aralkyl, in which the alkyl groups are linear or branched chain containing from 1 to 20 carbon atoms and wherein $R_1$ is pyridine, said compounds having solubilities of at least 2% by weight in essentially water-immiscible, liquid hydrocarbon solvents.

2. A compound of claim 1, wherein said liquid hydrocarbon solvent is selected from the group consisting of aliphatic and aromatic hydrocarbons and mixtures thereof, having flash points of at least 150° F. and the $Cu^{++}$ complexes thereof also have solubilities of at least 2% by weight in said liquid hydrocarbon solvents.

3. A compound of claim 1, wherein R is an alkyl, alkaryl or aralkyl, in which the alkyl group is a linear or branched chain alkyl containing at least eight carbon atoms.

4. A compound of claim 3, wherein R contains electron-withdrawing substituents selected from the group consisting of halogen, ester, nitro and nitrile.

5. A compound of claim 1, wherein R is dodecylbenzene.

6. 2-(dodecylbenzenesulfonylhydrazino)-pyridine.

7. A composition of matter consisting essentially of a solution of a sulfonylhydrazine in an essentially water-immiscible, liquid hydrocarbon solvent, said solution containing at least 2% by weight of said sulfonylhydrazine, said sulfonylhydrazine being selected from compounds of the structure:

wherein R is a member selected from the group consisting of alkyl, aryl, alkaryl and aralkyl, in which the alkyl groups are linear or branched chain containing from 1 to 20 carbon atoms and wherein $R_1$ is pyridine.

8. The composition of claim 7, wherein said solvent is selected from the group consisting of aliphatic and aromatic hydrocarbons and mixtures thereof, having flash points of at least 150° F. and the $Cu^{++}$ complexes of the sulfonylhydrazines have a solubility in said solvent of at least 2% by weight.

9. The composition of claim 7, wherein said solvent is selected from the group consisting of aliphatic and aromatic kerosenes, benzene, toluene and xylene.

10. The composition of claim 7, wherein said sulfonylhydrazine is present in an amount of about 2 to 75% by weight.

11. The composition of claim 7, wherein R is an alkyl, alkaryl or aralkyl, in which the alkyl group is a linear or branched chain alkyl containing at least eight carbon atoms.

12. The composition of claim 11, wherein R is dodecylbenzene.

13. The composition of claim 7, wherein said sulfonylhydrazine is 2-dodecylbenzenesulfonylhydrazino) pyridine.

14. The composition of claim 13, wherein said sulfonylhydrazine is present in an amount of from 25 to 75% by weight.

15. The composition of claim 7, wherein said composition additionally contains an amount of a metal complex of said sulfonylhydrazine and a metal ion selected from the group consisting of $Cu^{++}$, $Ni^{++}$, $Co^{++}$, $Co^{+++}$ and $Zn^{++}$.

16. The composition of claim 15, wherein the metal ion and the sulfonylhydrazine are present in a molar ratio up to about 1:2.

17. The composition of claim 15, wherein said metal ion is $Cu^{++}$.

* * * * *